(12) United States Patent
Tanaka et al.

(10) Patent No.: US 9,229,114 B2
(45) Date of Patent: Jan. 5, 2016

(54) RADIATION ANALYZER AND METHOD FOR ANALYZING RADIATION

(71) Applicant: HITACHI HIGH-TECH SCIENCE CORPORATION, Tokyo (JP)

(72) Inventors: Keiichi Tanaka, Tokyo (JP); Masataka Ohgaki, Tokyo (JP); Akikazu Odawara, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 65 days.

(21) Appl. No.: 13/965,673

(22) Filed: Aug. 13, 2013

(65) Prior Publication Data

US 2014/0048717 A1 Feb. 20, 2014

(30) Foreign Application Priority Data

Aug. 20, 2012 (JP) ................. 2012-181833

(51) Int. Cl.
*G01J 1/42* (2006.01)
*G01T 1/16* (2006.01)
*G01N 23/225* (2006.01)
*G01T 1/26* (2006.01)

(52) U.S. Cl.
CPC ............... *G01T 1/16* (2013.01); *G01T 1/1606* (2013.01); *G01N 23/225* (2013.01); *G01T 1/26* (2013.01)

(58) Field of Classification Search
CPC .......... G01T 1/26; G01T 1/16; G01N 23/223; G01N 23/225

USPC ............................................. 250/336.2, 337
See application file for complete search history.

(56) References Cited

U.S. PATENT DOCUMENTS

2010/0019152 A1* 1/2010 Tanaka et al. .............. 250/336.2

FOREIGN PATENT DOCUMENTS

JP 2009 271016 11/2009

OTHER PUBLICATIONS

Machine translation of Japanese Patent Application Publication No. 2009-271016A to Nakamaya et al.*

* cited by examiner

*Primary Examiner* — Mark R Gaworecki
*Assistant Examiner* — Kenneth J Malkowski
(74) *Attorney, Agent, or Firm* — Adams & Wilks

(57) ABSTRACT

A radiation analyzer includes a transition edge sensor for detecting radiation and a cold head that cools the transition edge sensor. A current detecting mechanism detects a current flowing in the transition edge sensor, and a peak analyzing unit measures a peak value based on the current detected by the current detecting mechanism. A first heater is configured to heat the cold head to keep a temperature of the transition edge sensor constant. A sensitivity correction operating unit is configured to correct a sensitivity of the transition edge sensor based on a relation obtained in advance between an output of the first heater and the peak value measured by the peak analyzing unit.

20 Claims, 11 Drawing Sheets

RADIATION ANALYZER AND METHOD FOR ANALYZING RADIATION

This application claims priority from Japanese Patent Application No. 2012-181833 filed on Aug. 20, 2012, the entire subject-matter of which is incorporated herein by reference.

BACKGROUND

1. Technical Field

The present invention relates to a radiation analyzer including a radiation detector provided with a transition edge sensor and to a method for analyzing radiation.

2. Related Art

There are radiation analyzers capable of energy discrimination of radiation such as an energy dispersive spectroscopy (EDS) and a wavelength dispersive spectroscopy (WDS).

The EDS is an X-ray detector that converts the energy of X-rays captured therein to an electric signal and derives the energy depending on the intensity of the electric signal. The WDS is an X-ray detector that monochromatizes X-rays (energy discrimination) with a spectroscope and detects the monochromat zed X-rays with a proportional counter tube.

Semiconductor detectors such as a silicon-lithium (SiLi) based detector, a silicon drift detector, and a germanium detector are known as EDSs. The silicon silicon-lithium based detector and the silicon drift detector are frequently used in the electron microscope of an elemental analyzer and are capable of detecting energy in a wide range of 0 to about 20 keV. However, their energy resolution cannot be readily improved to 130 eV or more and remains merely one-tenth or less of that of WDSs. This is because these detectors contain silicon, and thus their characteristics depend on the bandgap of silicon (about 1.1 eV) in principle.

Here, the energy resolution, which is one of the indexes indicating the performance of an X-ray detector, is described. The energy resolution of 130 eV means that detection can be done with uncertainty of about 130 eV when the X-ray detector is irradiated with X-rays. That is, the smaller the uncertainty is, the higher the energy resolution is. For example, in the case of detecting characteristic X-rays having two adjacent spectral lines with a difference of two adjacent peaks of about 20 eV, energy resolution of 20 to 30 eV is sufficient to separate the two peaks in principle because the uncertainty is reduced as the energy resolution is increased.

In recent years, demands for superconductive X-ray detectors of energy dispersion type having energy resolution equivalent to that of WDSs have been growing. A transition edge sensor (TES) among superconductive X-ray detectors is a high-sensitive thermometer utilizing a steep change in resistance ($\Delta R \cong 0.1\Omega$ at $\Delta T \cong$ a few mK) of a metallic thin film appearing at a transition between the superconductive state and the normal conductive state. Note that a TES is also referred to as a microcalorimeter.

The TES is used to analyze a sample by controlling the change of temperature in the TES in response to incident fluorescent X-rays or characteristic X-rays emitted from the sample irradiated with primary X-rays or primary electron beams. The TES has a higher energy resolution than that of other detectors. For example, it can achieve energy resolution of 10 eV or less with the characteristic X-rays of 5.9 keV.

A TES provided to a scanning electron microscope that includes an electron source such as a tungsten filament can capture characteristic X-rays emitted from a sample irradiated with electron beams and thus easily separate peaks of the characteristic X-rays (Si-K$\alpha$, W-M$\alpha$, $\beta$) that are difficult to separate by a semiconductor-based X-ray detector.

In X-ray analyzers including such superconductive X-ray detectors, an amplifier based on a superconducting quantum interference device (SQUID) is used to detect a small current variation in the TES. It is significant to keep a current flowing in the SQUID amplifier to achieve higher energy resolution of the TES. As described later, it is needed to reduce current variations in a current flowing in the SQUID amplifier to a small degree to provide higher energy resolution.

An X-ray analyzer is known as an apparatus that keeps a SQUID amplifier current, or a baseline TES current, constant. This X-ray analyzer corrects a current flowing in a TES or the peak value of the current, for example, depending on the fluctuation range of a baseline current flowing in the TES from a specific value if the baseline current deviates from the specific value and fluctuates (refer to JP-A-2009-271016).

The above-mentioned X-ray analyzer, however, requires constant monitoring of a baseline current. In the case where a TES detects no X-ray, a SQUID amplifier outputs a constant baseline value continuously. When the TES detects an X-ray, a signal pulse is superimposed on a baseline. When the number of X-rays is small, a period between one pulse and the next one is sufficiently long, and thus a baseline can be monitored in the period between the signal pulses. By contrast, when the number of X-rays is large, a period between one pulse and the next one is short, that is, the period is not enough to detect a baseline, and thus it is hard to monitor accurate baselines. Thus, there is a problem in that accurate determination of a baseline is difficult when a large number of signal pulses are detected.

SUMMARY

Therefore, illustrative aspects of the present invention provide a radiation analyzer and a method for analyzing radiation which are able to perform accurate sensitivity correction even if the number of signal pulses is large, resulting in provision of high energy resolution.

In view of the foregoing, one illustrative aspect of the present invention adopts the following configurations. A radiation analyzer according to one aspect of the present invention includes: a transition edge sensor configured to detect radiation; a current detecting mechanism configured to detect a current flowing in the transition edge sensor; a peak analyzing unit configured to detect a peak value based on the current detected by the current detecting mechanism; a first heater configured to heat the transition edge sensor to keep a constant temperature; and a sensitivity correction operating unit configured to correct sensitivity of the transition edge sensor based on a relation between an output of the first heater and the peak value measured by the peak analyzing unit which has been obtained in advance.

The radiation analyzer calculates and registers a correlation curve of a second thermometer, which is built in the TES, and a first thermometer in advance, and corrects sensitivity of a signal pulse using information associated with the first thermometer irrelevant to signal pulses. Thus, it is possible to perform sensitivity correction regardless of the counting rate of signal pulses and always provide a constant peak value of a signal pulse in response to characteristic X-rays having the same energy. As a result, high energy resolution can be obtained stably for a long term.

The radiation analyzer of the present invention may further include: a cold head configured to cool the transition edge sensor; and a first thermometer that is provided to the cold head. In the radiation analyzer of the present invention, the first heater may be configured to produce output to keep temperature measured by the thermometer constant.

In the radiation analyzer of the present invention, the cold head is provided with the first heater to keep the temperature or electric signal of the cold head constant; the sensitivity correction operating unit is provided with a function for associating a heater value with the sensitivity of the transition edge sensor; and a peak value is corrected online or offline. The radiation analyzer uses a heater value to keep the temperature of the cold head constant as information correlated to the first thermometer. Once the heater value is correlated to the sensitivity of the transition edge sensor, offline sensitivity or online sensitivity can be acquired by monitoring the heater value before signal pulses are obtained.

In the radiation analyzer of the present invention, the sensitivity correction operating unit may be provided with a function for repeating multiple times the following processes: monitoring the heater value at certain regular intervals; obtaining radiation having a specific energy for a predetermined period right after the latest heater value is monitored; and incorporating correlation data of a new heater value in association with new sensitivity in characteristics between the heater value and sensitivity having been obtained. In other words, in the radiation analyzer, the characteristics between the heater value and sensitivity are updated over time. Thus, more accurate characteristics between the heater value and sensitivity can be obtained. It is therefore possible to provide a more reliable radiation analyzer having high energy resolution.

In the radiation analyzer of the present invention, the first thermometer may contain a semiconductor or a superconductor. This radiation analyzer indicates accurate temperature constantly with a thermometer having a sufficient sensitivity in a cryogenic temperature range about 100 mK, thereby outputting a reliable heater value. It is therefore possible to perform more precise correction.

The radiation analyzer of the present invention may include a second heater configured to heat the transition edge sensor to keep a constant temperature.

That is, the radiation analyzer of the invention includes the first heater and the second heater for adjusting power values in the cold head. The power of the first heater can be adjusted through power adjustment of the second heater. Thus, it is easy to obtain correlation of the heater value and sensitivity of the first heater. It is therefore possible to perform more precise correction.

A method for analyzing radiation according to another aspect of the present invention includes: heating a transition edge sensor with a first heater and measuring a peak value based on a current flowing in the transition edge sensor to generate correlation data of an output of the first heater and the peak value; detecting radiation with the transition edge sensor heated with the first heater and measuring the peak value of the radiation based on a current flowing in the transition edge sensor; correcting sensitivity of the transition edge sensor using the output of the first heater and the correlation data at the detecting; and obtaining energy spectrum of the radiation using the corrected sensitivity and the peak value of the radiation.

In the method for analyzing radiation of the present invention, the first heater or a second heater may be heated to keep the temperature of the transition edge sensor constant.

The radiation analyzer and the method for analyzing radiation according to the present invention are able to correct sensitivity regardless of the counting rate of signal pulses, and thus to obtain a constant peak value for a signal pulse in response to characteristic X-rays having the same energy. As a result, high energy resolution can be obtained stably for a long term.

DETAILED DESCRIPTION OF PREFERRED EMBODIMENTS

The following describes the operating principle of an embodiment of the present invention. In the operation of detecting radiation, a TES 1 utilizes a superconducting transition edge of a superconductor. The TES 1 holds an operating point in the superconducting transition edge between normal conductivity and superconductivity. Thus, in the case where the TES 1 absorbs radiation once and holds the operating point in the superconducting transition edge, the resistance change of several micro watts can be obtained with a temperature change of 100 mK, obtaining a radiation pulse in the order of micro angstrom.

The relation between a pulse peak value and radiation energy is obtained in advance. That makes it possible to detect the energy of radiation applied to the TES 1 based on the peak value of the signal pulse even if the energy of the radiation is unknown.

The operating point of the TES 1 is determined in accordance with a thermal balance between a current flowing in the TES 1 (hereinafter, referred to as a TES current) and a heat link to a heat storage tank provided in the TES 1 so as to hold the TES 1 in the operating point in the superconducting transition edge. The energy resolution of the TES 1 is a function of temperature, and thus it is preferred to decrease the temperature as low as possible. In this embodiment, the temperature of the heat storage tank is set in a range from about 50 mK to 400 mK. The TES current is determined by Equation 1:

$$I_t^2 R_t = G(T - T_b)$$ (Equation 1)

where Rt is the operating resistance of the TES 1, G is the thermal conductivity of a heat link thermally connecting a second thermometer 17 provided to the TES 1 with the heat storage tank, T is the temperature of the second thermometer 17, and Tb is the temperature of the heat storage tank.

The relation between the TES current It and a pulse peak value ΔI is represented by Equation 2:

$$I_t = \frac{CT}{\alpha E}\Delta I \quad \text{(Equation 2)}$$

where α is the sensitivity of the TES 1, C is a heat capacity, and E is the energy of applied radiation. If the TES current It is constant, the pulse peak value ΔI is kept constant ideally.

Equation 2 shows that the peak value of a signal pulse corresponding to radiation having the same energy applied to the TES 1 changes as the baseline current flowing in the TES 1 changes. Equation 1 shows that a baseline current flowing in the TES changes as the temperature of the heat storage tank changes. That is, a change in the heat storage tank changes a pulse peak value, thereby deteriorating the energy resolution.

Figure 1:
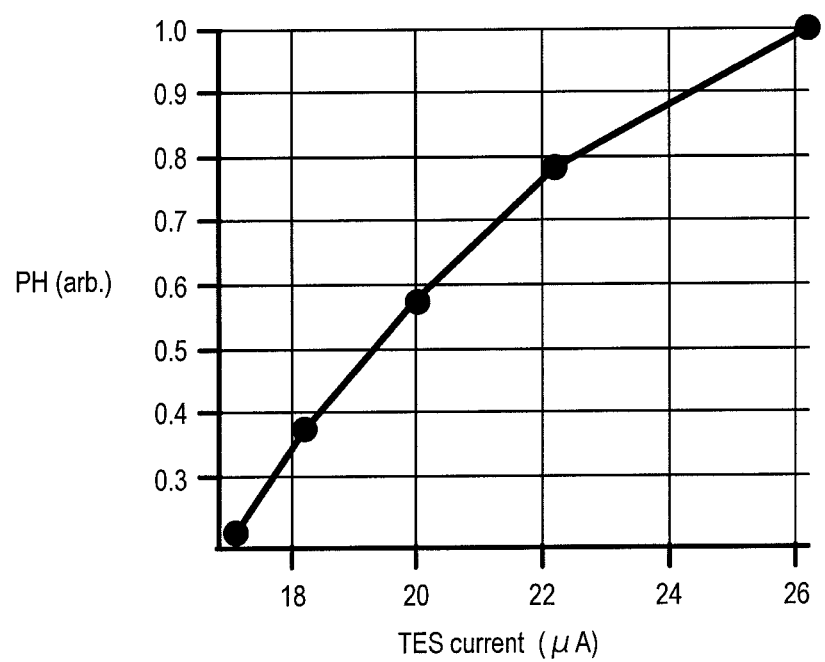
FIG. 1 is a graph illustrating a relation between a pulse peak value and a TES current in an embodiment of the present invention.

FIG. 1 illustrates a relation between a pulse peak value obtained while a bias current applied to the TES 1 changes and a current flowing in a SQUID amplifier 11 (equal to the TES current It). As illustrated in this graph, the pulse peak value increases as the TES current increases in accordance with Equation 2. A calculation result of convolution of the pulse signal and a band filter is output to a personal computer as an example of a pulse peak value.

In this case, on a display of the personal computer, a spectrum display screen is displayed with the transverse as pulse peak values and the ordinate as counts. For example, when the pulse peak value is 100, the count at a scale of 100 is incremented by one. Repeating the process produces radiation spectrum.

This means that if the output value after being filtered changes even the energy is the same, the pulse peak value varies. The degree of the variation corresponds to the energy resolution. Thus, it is needed to reduce the variation in the pulse peak value in response to the same energy to achieve high energy resolution.

For example, the pulse peak value varies as a current flowing in the SQUID amplifier 11 changes. To achieve high energy resolution, as described above, it is significant to keep the current in the SQUID amplifier 11 constant, or provide means for keeping the pulse peak value constant in the case where a current flowing in the SQUID amplifier 11 changes.

Next, one embodiment of the radiation analyzer of the present invention is described with reference to FIGS. 2 to 11.

Figure 2:
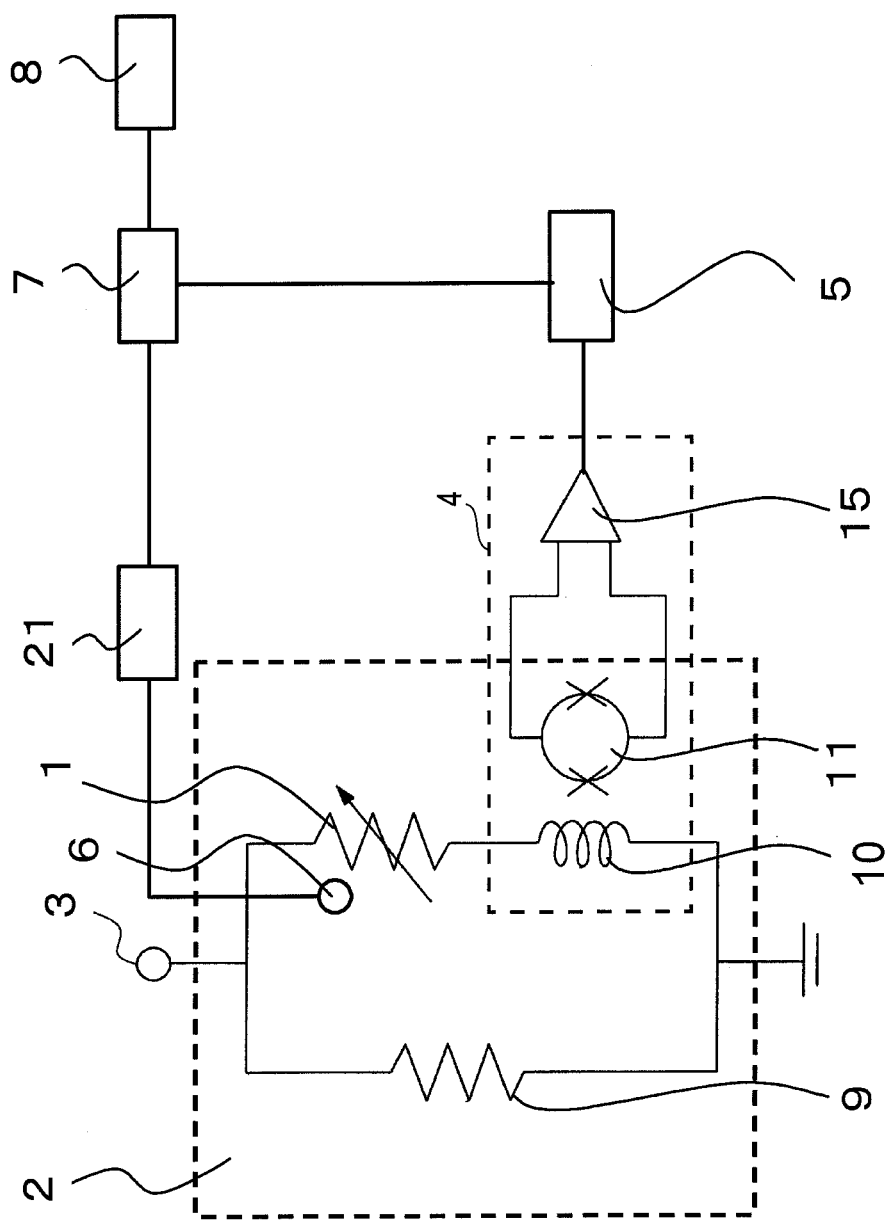
FIG. 2 is a configuration diagram illustrating a radiation analyzer in the embodiment of the present invention.

The radiation analyzer of the embodiment is an apparatus applicable to a composition analyzer such as an electron microscope, ion microscope, X-ray microscope, and X-ray fluorescence spectrometer. As illustrated in FIG. 2, the radiation analyzer includes: a sensor circuit unit 2 provided with the TES 1 that receives radiation and detects the energy of the radiation as a temperature change to output an electric signal representing the detection result; a bias current source 3 that applies a constant voltage to the sensor circuit unit 2 to supply a bias current; a current detection mechanism 4 that detects a current flowing in the TES 1; a peak analyzing unit 5 that measures the peak value of the detected signal pulse; a first thermometer 6 that is built in a stage to mount the sensor circuit unit 2 thereon and measures the temperature of the TES 1; a sensitivity correction operating unit 7 for correcting the peak value of the signal pulse from a peak analyzing unit 5 on the basis of temperature data output from the first thermometer 6; and a spectrum display 8 for displaying spectrum thereon in response to the signal pulse subjected to sensitivity correction.

The sensor circuit unit 2 includes: a shunt resistor 9 having a resistance smaller than that of the TES 1 and connected in parallel with the TES 1; and the SQUID amplifier 11 provided with an input coil 10 connected in series with the TES 1.

Figure 3:
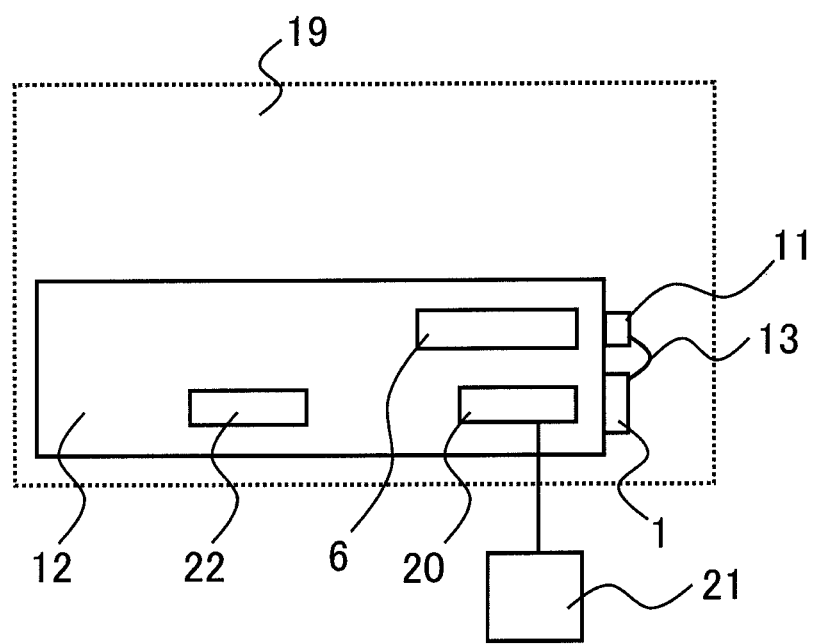
FIG. 3 is a configuration diagram illustrating a detector in the embodiment of the present invention.
Figure 4:
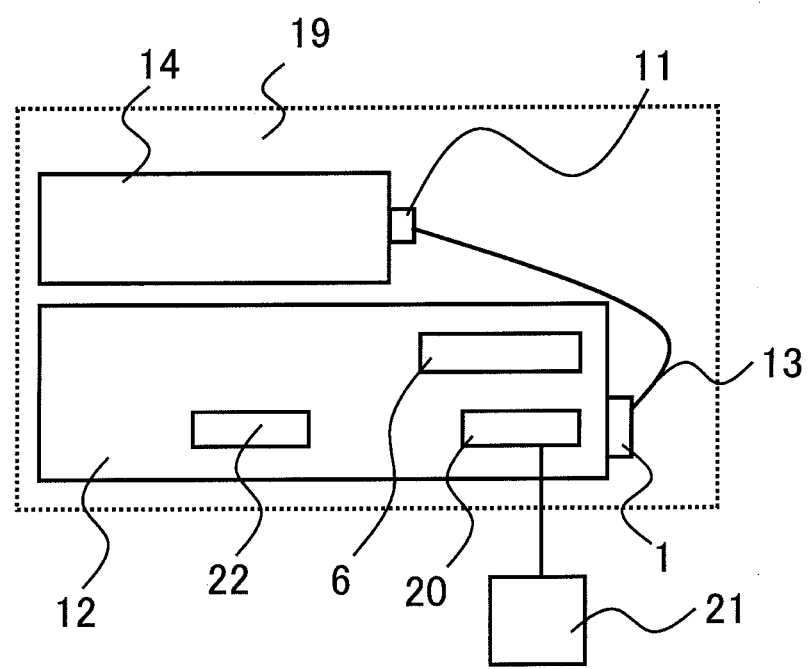
FIG. 4 is a configuration diagram illustrating another detector in the embodiment of the present invention.

As illustrated in FIG. 3, the TES 1, the shunt resistor 9, and the SQUID amplifier 11 are mounted on a tip of a cold head 12 cooled down to a range from 50 mK to 400 mK in a refrigerator. The TES 1 and the SQUID amplifier 11 are connected through a superconductive wire 13. In another example illustrated in FIG. 4, the TES 1 is mounted on a tip of the cold head 12 and the SQUID amplifier 11 is mounted on a tip of a cold block 14 cooled down to 9 K or lower. Note that the shunt resistor 9 is not illustrated in FIG. 3 or 4.

In the sensor circuit 2, when the bias current source 3 supplies a bias current, the current is divided in accordance with a resistance ratio of the resistance of the shunt resistor 9 to the resistance of the TES 1. That is, the voltage of the TES 1 is determined on the basis of a current flowing in the shunt resistor 9 and a voltage specified with the resistance of the shunt resistor 9.

The current detection mechanism 4 includes: the SQUID amplifier 11 incorporating the input coil 10; and a room temperature amplifier 15 for amplifying and shaping an electric signal output from the SQUID amplifier 11. The peak analyzing unit 5 classifies an output signal from the room temperature amplifier 15 in accordance with the peak value in voltage of the output signal. In this embodiment, the room temperature amplifier 15 and the SQUID amplifier 11 incorporating the input coil 10 are used as the current detection mechanism 4; however, any other configuration can be adopted as long as it can detect a change in current flowing in the TES 1.

The peak analyzing unit 5 is a multi-channel pulse height analyzer that obtains a pulse peak value (voltage) from the output signal (e.g., a radiation pulse signal in the case where the TES 1 is irradiated with radiation) sent from the room temperature amplifier 15 to generate energy spectrum. The peak analyzing unit 5 reads the peak value of a radiation pulse and increments the count corresponding to the peak value by one in a histogram having the ordinate as counts and the transverse as peak values. The peak analyzing unit 5 repeats the same process on multiple radiation signal pulses. In addition, the peak analyzing unit 5 has a function for generating a histogram and displaying it on a spectrum display unit 8 when sensitivity correction described later is not performed. In the case that the peak analyzing unit 5 or the spectrum display unit 8 is provided in advance with correction data for conversion from a signal pulse voltage to energy, spectrum can be displayed with the ordinate as counts and the transverse as energy.

The first thermometer 6 is provided in the cold head 12 and monitors the temperature of the cold head 12. Semiconductors, superconductors, or metallic oxides can be material of the first thermometer 6. For example, ruthenium oxide and germanium can be used for the first thermometer 6. The first thermometer 6 changes its resistance as the temperature of the cold head 12 changes, and thus it is possible to measure a temperature by associating the temperature and an electric signal (typically, a voltage signal) output from the first thermometer 6 in advance. The temperature status of the cold head 12 can be determined using the temperature when the temperature and resistance are associated in advance or using the electric signal directly when the temperature and resistance are not associated with each other.

The sensitivity correction operating unit 7 is a mechanism that receives a signal pulse output from the room temperature amplifier 15 and temperature data or an electric signal from the first thermometer 6 to correct the peak value of the signal pulse. The sensitivity correction operating unit 7 includes operating circuits for performing the above-mentioned correction processing, a memory, and other components. The sensitivity correction operating unit 7 can be configured as a software process executed on a personal computer or configured as dedicated hardware. The sensitivity correction operating unit 7 may be built in the peak analyzing unit 5 or the spectrum display unit 8 and integrated therewith. A specific method for sensitivity correction is described later.

Figure 5:
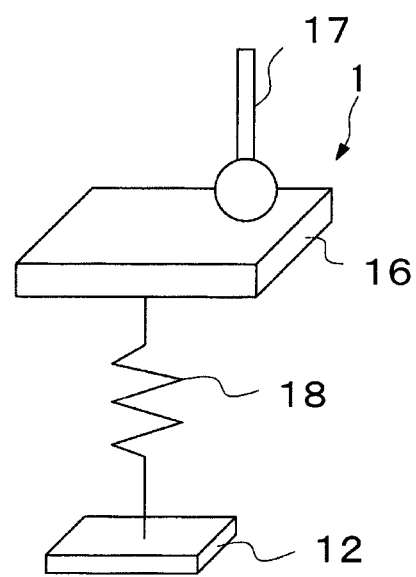
FIG. 5 is a conceptual diagram illustrating a TES in the embodiment of the present invention.

As illustrated in FIG. 5, the TES 1 includes: an absorbing body 16 that is made from a metallic band, a semimetal, or a semiconductor body for absorbing X-rays; a second thermometer 17 that is made from a superconductor body and detects heat generated in the absorbing body 16 as a temperature change; and a membrane 18 that loosely connects the second thermometer 17 thermally to the cold head 12 and controls a flow rate of heat drifted to the heat storage tank (not illustrated). For example, aluminum can be used for the absorbing body 15, a material including a titanium layer and a gold layer for the second thermometer 17, and silicon nitride for the membrane 18 and the heat storage tank.

Joule heat generated in the second thermometer 17 and heat drifted from the second thermometer 17 (or the absorbing body 16) to the cold head 12 through the membrane 18 are thermally balanced to hold the resistance of the TES 1 in the superconducting transition edge between normal conductivity and superconductivity.

The thermal balance of the Joule heat and the heat drifted through the membrane 18 is represented by Equation 1. In practice, however, Equation 1 cannot determine the TES current that is affected by thermal variation from the outside of the TES 1. Equation 1 can be modified as Equation 3 by introducing Pex. representing thermal variation from the outside of the TES 1:

$$I_t^2 R_t(T) + \left(V + \frac{GT}{I\alpha}\right)\delta I_t + P_{ex.} = G(T - T_b) \quad \text{(Equation 3)}$$

where $\alpha$ is the sensitivity of the TES sensor.

To satisfy Equation 3, the second term $\delta I t$ on the left side of Equation 3 reduces as Pex. increases. The following exemplifies heat variation from the outside: heat variation in the cold head 12 cooling the TES 1; radiant heat variation due to heat variation in a heat shield 19 surrounding the cold head 12; and heat variation in the heat shield 19 due to heat conduction from the heat shield 19 to the TES 1 through gas remaining in the refrigerator.

FIG. 1 is an example of a graph illustrating a relation between a pulse peak value (PH) and a current flowing in the TES 1. The pulse peak value increases monotonously as the current flowing in the TES 1 increases in accordance with Equation 2. That is, it is significant to keep a current in the TES 1 constant in order to keep the pulse peak value constant.

The TES 1 needs to be cooled down to about 100 mK. There is such cooling means as a dilution refrigerator and adiabatic demagnetization refrigerator (ADR). The dilution refrigerator relates to a cooling technique using difference in enthalpy appearing when 3He in the concentration phase dissolves into the dilute phase. The ADR relates to a technique to cool an object connected to a magnetic body using an increase in entropy caused by removing a magnetic field applied to the magnetic body to align the directions of spins. In each of the refrigerators, the cold head 12 is mounted on the most cooled position. In the dilution refrigerator and the ADR, the first thermometer 6 for measuring temperature is provided to the cold head 12. The temperature information of the cold head 12 can be obtained by monitoring an electric signal (typically, a voltage signal) output from the first thermometer 6. A temperature can be determined in a real time using a relation between an electric signal and a temperature registered in advance in a temperature controller 21. The temperature controller 21 is placed between the first thermometer 6 and the sensitivity correction operating unit 7 and has a function to send the temperature data or the electric signal obtained in the first thermometer 6 to the sensitivity correction operating unit 7.

To keep the temperature of the cold head 12 in the dilution refrigerator constant, a first heater 20 is provided. The first heater 20 is connected with the temperature controller 21. When the temperature controller 21 sets a target temperature, the temperature controller 21 controls the output of the first heater 20 on the basis of the temperature data or the electric signal from the first thermometer 6. By contrast, the ADR keeps the temperature of the cold head 12 by controlling the intensity of a magnetic field applied to the magnetic body on the basis of the temperature data or the electric signal from the first thermometer 6. The following describes a method for correcting sensitivity with the dilution refrigerator, but the same method can be applied to the ADR.

As represented by Equations 1 and 2, the pulse peak value increases as the temperature of the heat storage tank decreases, and the pulse peak value decreases as the temperature of the heat storage tank increases. The first thermometer 6 monitors the temperature of the heat storage tank. The output of the first heater 20 is regulated to keep the temperature measured by the first thermometer 6 constant.

Figure 6:
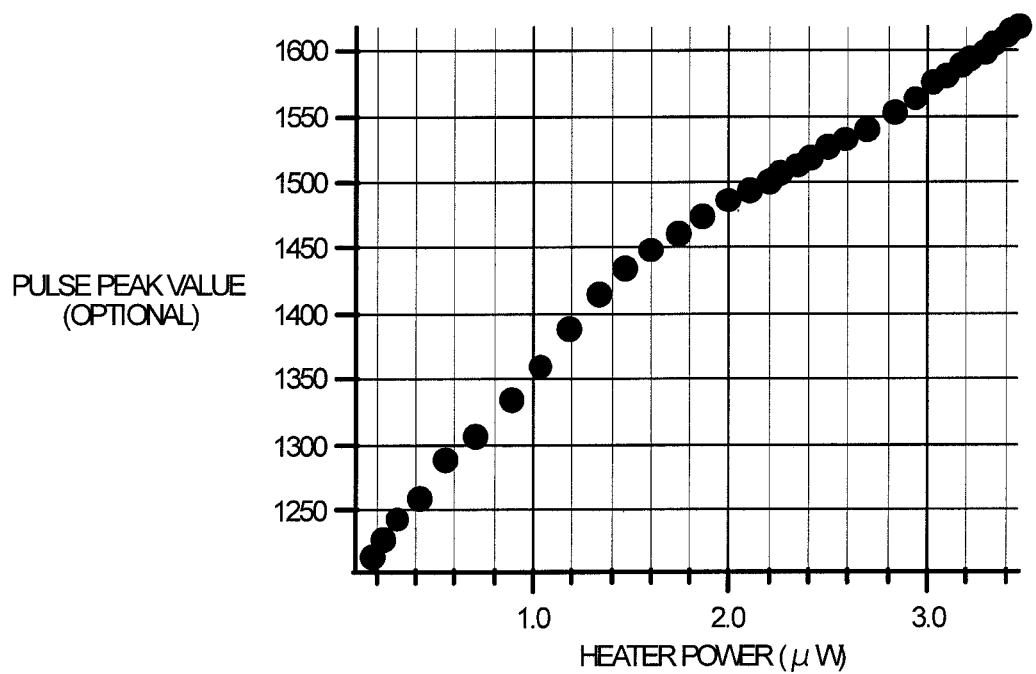
FIG. 6 is a graph illustrating a relation between a pulse peak value and a heater value in the embodiment of the present invention.
Figure 7:
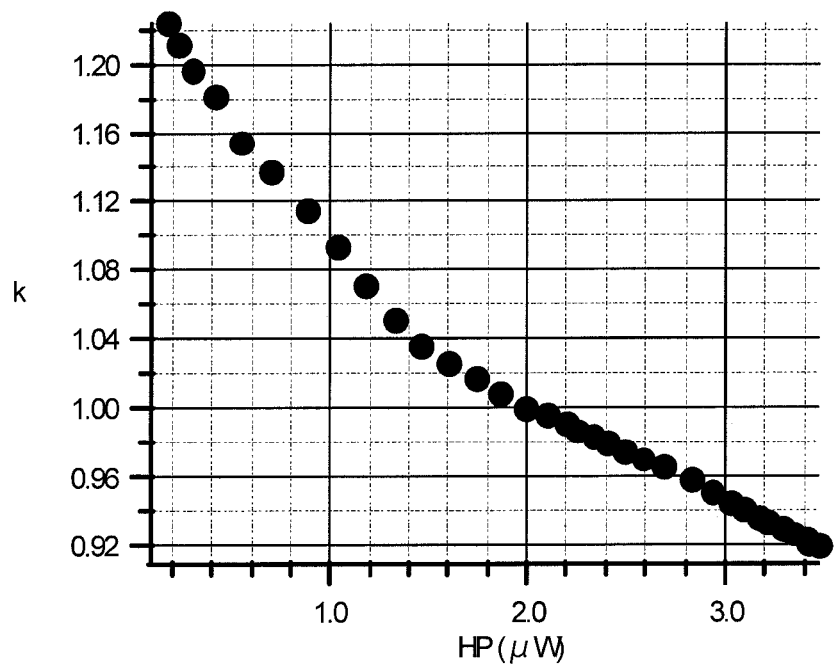
FIG. 7 is a graph illustrating a relation between a sensitivity correction factor and a heater value in the embodiment of the present invention.
Figure 8:
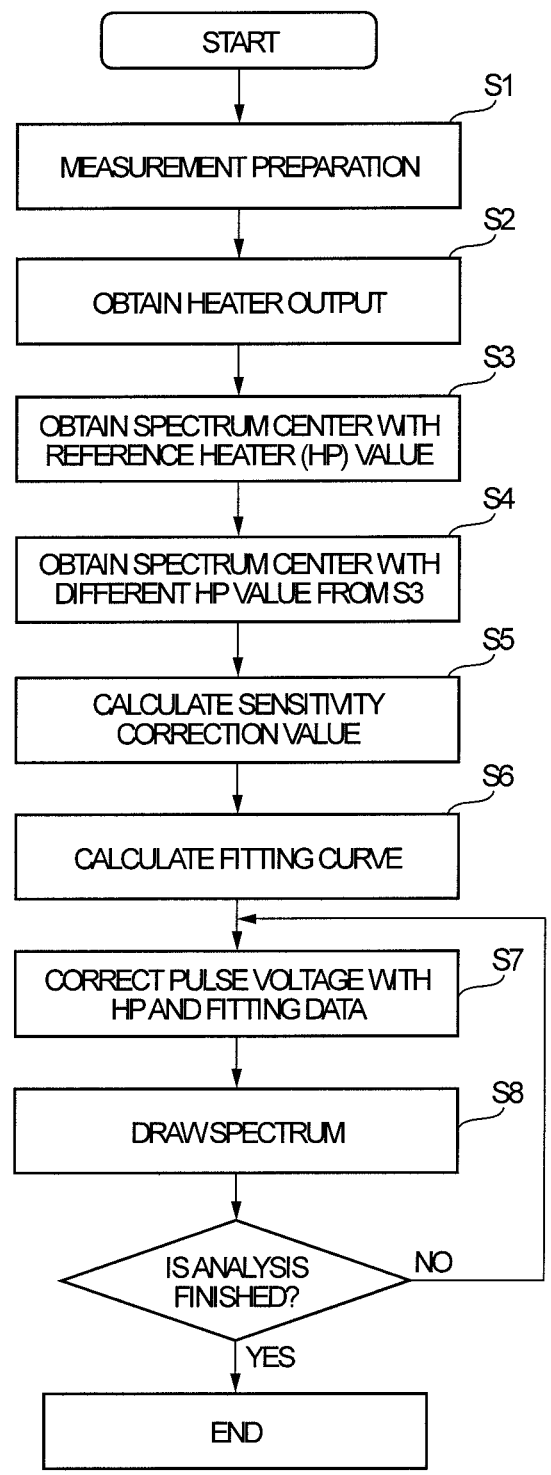
FIG. 8 is a flowchart of the embodiment of the present invention.

The output of the first heater 6 and the peak value of a signal pulse have a relation illustrated in FIG. 6. The ordinate shows the peak value of a signal pulse and the transverse shows a heater value. The output of the first heater 20 is controlled constantly to keep the temperature measured by the first thermometer 6 constant. As mentioned previously, the heater value changes because of the heat penetration from the outside, for example. The pulse peak value of a certain heater value is defined as a reference. The pulse peak value is divided by the reference to obtain a result (sensitivity correction value). A relation between the sensitivity correction value and the output of the first heater 20 slopes downward to the right as illustrated in FIG. 7. Once the characteristics in FIG. 7 are obtained, an accurate pulse peak value can be obtained by operating the correction value for correcting a pulse in the output of the heater to the obtained pulse peak value. This process is described below with reference to the flowchart in FIG. 8.

After a refrigerator is sufficiently cooled, the temperature controller 21 receives temperature data or an electric signal to control the output of the first heater 20 so that a predetermined temperature or an electric output value is achieved. After the heater output is stabilized, radiation having known energy is applied to the TES 1 to obtain signal pulses. For example, the known energy is an Al-K $\alpha$ ray of 1487 eV. In an electron microscope including therein a radiation detecting system, measurement preparation with an aluminum sample is arranged to detect a large number of signals of 1487 eV in a short period by using electron beams with acceleration voltages of 1.5 kV or more and selecting an appropriate current value (S1).

The temperature controller 21 updates the heater value in a second order. The sensitivity correction operating unit 7 obtains a heater output from the temperature controller 21 at certain regular intervals (S2). After detecting the latest heater value, the temperature controller 21 obtains signal pulses from the current detection mechanism 4 from the SQUID amplifier 11 for a predetermined period. The spectrum in FIG. 9 for example can be obtained when multiple signal pulses are obtained. The center of the spectrum is a signal pulse output corresponding to the heater value having been obtained. Visual confirmation or Gaussian fitting can be used to read the spectrum center. For example, a signal pulse voltage is assumed 100.000 mV when the heater value is 1.57 μW. Here, the applied radiation has the known energy, and thus it is defined that the output is 1487 eV at a heater value of 1.57 μW (S3).

Figure 9:
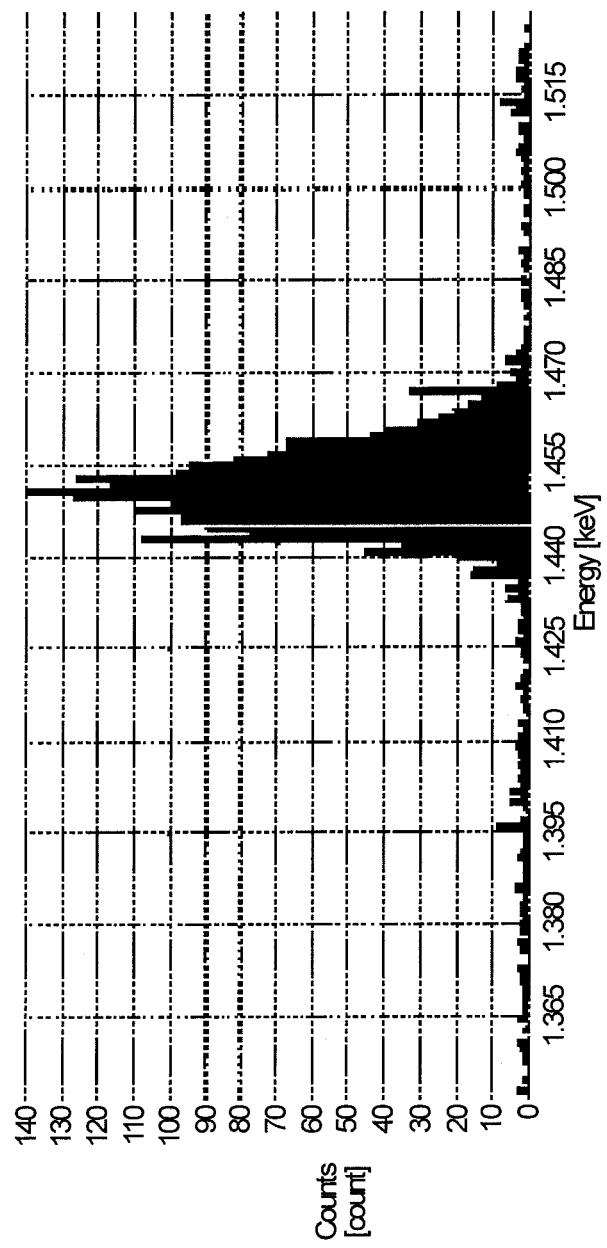
FIG. 9 is a spectrography of an Al-Kα ray in the embodiment of the present invention.

Sensitivity correction (k) values are determined on the basis of a reference heater (HP) value of 1.57 μW. Subsequently, the spectrum illustrated in FIG. 9 is obtained after a certain time has passed and the sensitivity correction operating unit 7 receives the latest HP value from the temperature controller 21. For example, the spectrum center is 101.015 mV when the HP value is 1.7258 μW. In this manner, relations between a plurality of HP values and spectrum centers are obtained in order to increase the accuracy of the correction (S4).

Figure 10:
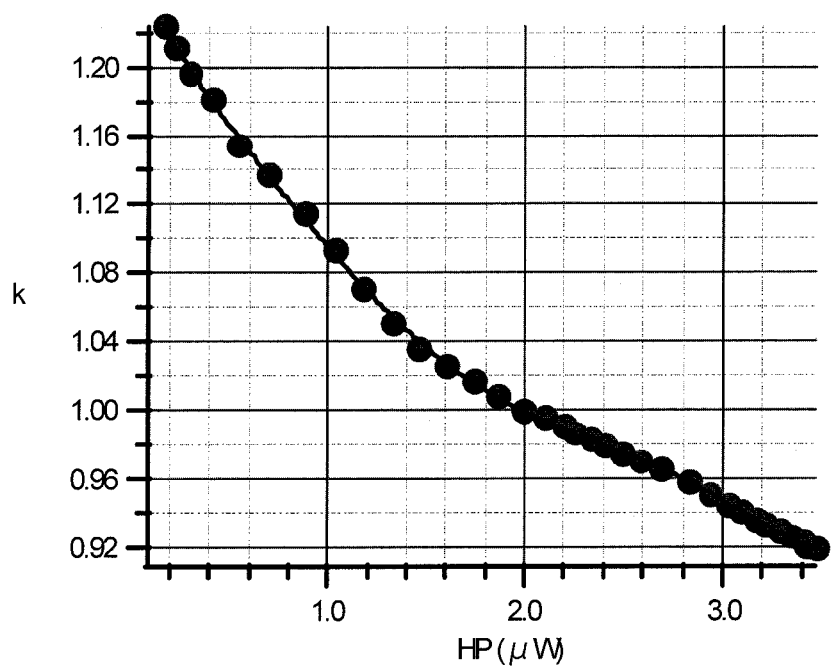
FIG. 10 is a graph illustrating a relation between a sensitivity correction factor and a heater value subjected to fitting in the embodiment of the present invention.

Next, the sensitivity correction (k) values are determined from the obtained spectrum centers. Each of the k values is obtained by dividing the output 100.000 mV at the reference of 1.57 μW by the corresponding spectrum center. That is, in the case where the spectrum center is 101.015 mV, the k value is: 100.000/101.015=0.989953 (S5). In this manner, the k values and HP values are obtained to be plotted on a graph. A fitting curve is calculated based on the obtained data. An n-th order function (n is an integer) and spline function can be used to calculate the curve (S6). FIG. 10 illustrates a result of the fitting using a seventh order function.

Figure 11:
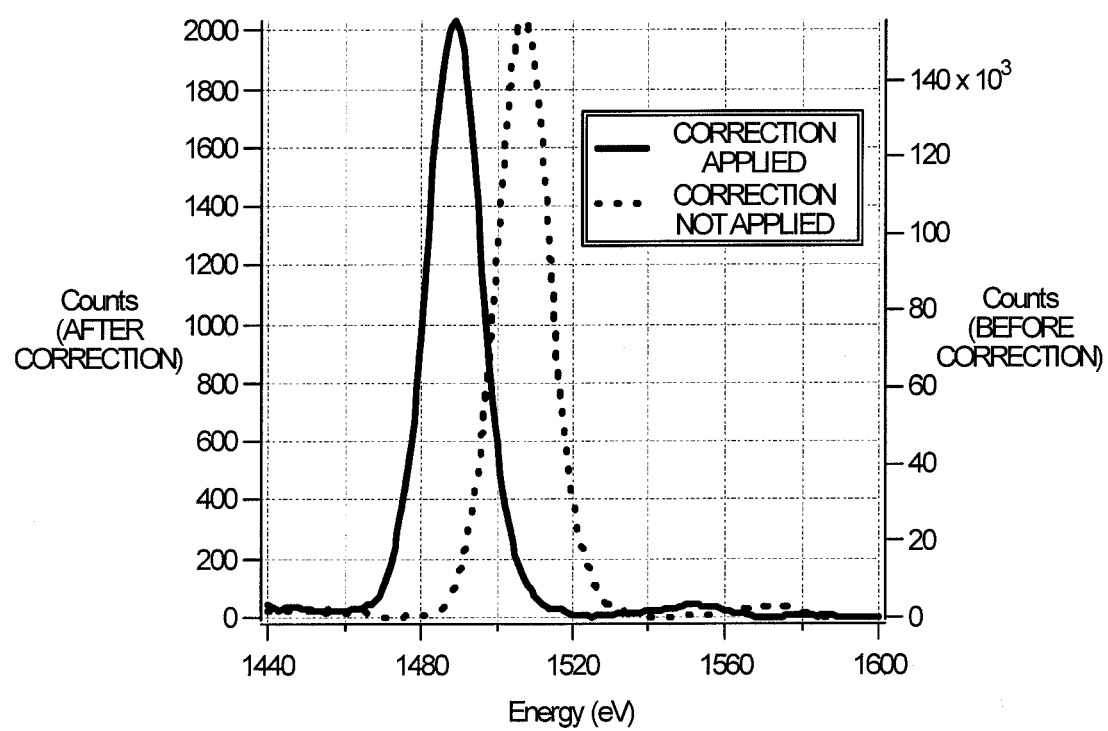
FIG. 11 is spectrum of the embodiment of the present invention.

To obtain actual spectrum, the sensitivity correction operating unit 7 regularly monitors the latest HP value the temperature controller 21 obtained, calculates the k values corresponding to the HP values from the seventh order function in. FIG. 10, and performs operation of the k values with the signal pulses output from the peak analyzing unit 5. The spectrum display unit 8 increments the count at the corrected signal pulse voltage by one (S7). In the case where the sensitivity correction operating unit 7 is provided with a function to convert a signal pulse voltage to energy in advance, spectrum with the transverse of the spectrum display unit as energy can be obtained. FIG. 11 illustrates spectrum data and represents the effect of a correction function. When the correction function is applied, the spectrum center is near 1487 eV. When the correction function is not applied, the spectrum center is near 1510 eV. When a spectrum covers a range including 1510 eV, naturally, it cannot be determined as radiation of A1, breaking the reliability of the spectrum. Repeating steps S7 and S8 until the analysis is finished achieves an analysis with high energy resolution without variation in the signal pulse voltage during the analysis.

It is also possible to interrupt the analysis in step S8 and return to step S2 in order to add other sensitivity correction data.

In this manner, the radiation analyzer of the present embodiment calculates and registers a correlation curve to be registered of the second thermometer 17 built in the TES 1 and the first thermometer 6 in advance, and corrects the sensitivity of a signal pulse using information associated with the first thermometer 6 irrelevant to signal pulses. Thus, it is possible to perform sensitivity correction regardless of the counting rate of signal pulses and always provide a constant peak value of a signal pulse in response to characteristic X-rays having the same energy. As a result, high energy resolution can be obtained stably for a long term.

This radiation analyzer uses a heater value for keeping the temperature of the cold head 12 constant as information correlated to the first thermometer 6. Once the heater value is correlated to the sensitivity of the TES, offline sensitivity or online sensitivity can be acquired by monitoring the heater value before signal pulses are obtained.

In this radiation analyzer, the characteristics between the heater value and sensitivity are updated over time. Thus, more accurate characteristics between the heater value and sensitivity can be obtained. It is therefore possible to provide more reliable, high energy resolution.

This radiation analyzer indicates accurate temperature constantly with a thermometer having a sufficient sensitivity in a cryogenic temperature range about 100 mK, thereby outputting reliable heater values. It is therefore possible to perform more precise correction.

The second heater 22 can be built in the cold head to obtain a sensitivity-heater value (k-HP) curve efficiently. The output of the first heater 20 balances with the cooling capacity of the cold head 12 thermally. When the output of the second heater 22 is added thereto, the output of the first heater 20 decreases because the cooling capacity of the cold head 12 is constant. That is, it is possible to control the power of the first heater 20 intentionally.

The present invention is not limited to the aforementioned embodiments, and various modifications can be made without departing from the scope of the present invention.

What is claimed is:

1. A radiation analyzer comprising:
    a transition edge sensor configured to detect radiation;
    a cold head configured to cool the transition edge sensor;
    a current detecting mechanism configured to detect a current flowing in the transition edge sensor;
    a peak analyzing unit configured to measure a peak value based on the current detected by the current detecting mechanism;
    a first heater configured to heat the cold head to keep a temperature of the transition edge sensor constant; and
    a sensitivity correction operating unit configured to correct a sensitivity of the transition edge sensor based on a relation obtained in advance between an output of the first heater and the peak value measured by the peak analyzing unit.

2. The radiation analyzer according to claim 1, further comprising:
    a thermometer provided to the cold head and configured to measure a temperature of the cold head.

3. The radiation analyzer according to claim 2,
    wherein the first heater is configured to produce the output to keep the temperature measured by the thermometer constant.

4. The radiation analyzer according to claim 2,
    wherein the thermometer comprises a semiconductor, superconductor, or metallic oxide.

5. The radiation analyzer according to claim 1, further comprising:
    a second heater configured to heat the cold head heated by the first heater to keep the temperature of the transition edge sensor constant.

6. The radiation analyzer according to claim 1, further comprising: a thermometer provided to the cold head for measuring a temperature of the cold head; and a temperature controller for controlling the output of the first heater to maintain the temperature measured by the thermometer constant.

7. The radiation analyzer according to claim 6, wherein the temperature controller is placed between the thermometer and the sensitivity correction operating unit and is configured to send temperature data obtained in the first thermometer to the sensitivity correction operating unit.

8. The radiation analyzer according to claim 1, further comprising a second heater configured to control the output of the first heater to keep the temperature of the transition edge sensor constant.

9. The radiation analyzer according to claim 1, wherein the transition edge sensor is mounted directly to the cold head.

10. A method for analyzing radiation comprising:
cooling with a cold head a transition edge sensor configured to detect radiation;
heating the cold head with a first heater and measuring a peak value based on a current flowing in the transition edge sensor to generate correlation data of an output of the first heater and the peak value;
detecting radiation with the transition edge sensor and measuring the peak value of the radiation based on a current flowing in the transition edge sensor;
correcting a sensitivity of the transition edge sensor using the output of the first heater and the generated correlation data; and
obtaining an energy spectrum of the detected radiation using the corrected sensitivity of the transition edge sensor and the measured peak value of the radiation.

11. The method for analyzing radiation according to claim 10,
wherein the cold head is heated with the first heater to keep the temperature of the transition edge sensor constant at the measuring of the peak value of the radiation.

12. The method for analyzing radiation according to claim 10,
wherein the cold head that is heated by the first heater is heated by a second heater to keep the temperature of the transition edge sensor constant at the measuring of the peak value of the radiation.

13. A radiation analyzer comprising:
a transition edge sensor configured to detect radiation;
a cold head configured to cool the transition edge sensor;
a first heater configured to heat the cold head so that a cooling capacity of the cold head and resulting temperature of the transition edge sensor are maintained constant;
a current detecting mechanism configured to detect a current flowing in the transition edge sensor;
a peak analyzing unit configured to measure a peak value based on the current detected by the current detecting mechanism; and
a sensitivity correction operating unit configured to correct a sensitivity of the transition edge sensor based on a relation obtained in advance between an output of the first heater and the peak value measured by the peak analyzing unit.

14. The radiation analyzer according to claim 13, further comprising a second heater configured to heat the cold head so as to decrease the output of the first heater while the cooling capacity of the cold head and resulting temperature of the transition edge sensor are maintained constant.

15. The radiation analyzer according to claim 14, wherein the second heater is built in the cold head.

16. The radiation analyzer according to claim 13, further comprising a second heater for heating the cold head so as to control the output of the first heater to maintain the cooling capacity of the cold head and resulting temperature of the transition edge sensor constant.

17. The radiation analyzer according to claim 13, further comprising: a thermometer provided to the cold head for measuring a temperature of the cold head; and a temperature controller for controlling the output of the first heater to maintain the temperature of the cold head measured by the thermometer constant.

18. The radiation analyzer according to claim 17, wherein the temperature controller is placed between the thermometer and the sensitivity correction operating unit and is configured to send temperature data obtained in the thermometer to the sensitivity correction operating unit.

19. The radiation analyzer according to claim 17, wherein thermometer is made of a semiconductor, superconductor, or metallic oxide.

20. The radiation analyzer according to claim 13, wherein the transition edge sensor is mounted directly to the cold head.

* * * * *